United States Patent [19]

Vanarthos

[11] Patent Number: 5,713,861
[45] Date of Patent: Feb. 3, 1998

[54] TRAUMA URETHRAL CATHETER AND METHOD OF USING SAME

[76] Inventor: William Vanarthos, 670 Gingermill La., Lexington, Ky. 40509

[21] Appl. No.: 645,131

[22] Filed: May 13, 1996

Related U.S. Application Data

[63] Continuation of Ser. No. 325,107, Oct. 17, 1994, abandoned.

[51] Int. Cl.⁶ .................................................. A61M 29/00
[52] U.S. Cl. .............................. 604/96; 604/101; 604/53
[58] Field of Search .............................. 604/96, 97, 101, 604/103, 104, 99, 93, 264, 280, 282; 606/192, 194

[56] References Cited

U.S. PATENT DOCUMENTS

| | | | |
|---|---|---|---|
| 2,799,273 | 7/1957 | Oddo | 604/101 |
| 2,936,760 | 5/1960 | Gants | 604/101 |
| 3,394,705 | 7/1968 | Abramson | 604/104 |
| 4,180,076 | 12/1979 | Betancourt | 604/101 |
| 4,350,161 | 9/1982 | Davis, Jr. | |
| 4,571,241 | 2/1986 | Christopher | 604/104 |
| 4,579,554 | 4/1986 | Glassman | |
| 4,610,662 | 9/1986 | Weikl et al. | 604/53 |
| 4,660,560 | 4/1987 | Klein | 604/101 |
| 4,671,795 | 6/1987 | Mulchin | 604/281 |
| 4,705,502 | 11/1987 | Patel | 604/49 |
| 4,762,125 | 8/1988 | Leiman et al. | |
| 4,781,677 | 11/1988 | Wilcox | |
| 4,790,809 | 12/1988 | Kuntz | 604/280 |
| 4,824,436 | 4/1989 | Wolinsky | 604/53 |
| 4,930,496 | 6/1990 | Bosley, Jr. | 604/101 |
| 4,968,307 | 11/1990 | Dake et al. | 604/264 |
| 4,976,692 | 12/1990 | Atad | 604/101 |
| 5,015,232 | 5/1991 | Maglinte | 604/96 |
| 5,059,178 | 10/1991 | Ya | 604/101 |
| 5,090,960 | 2/1992 | Don Michael | 604/96 |
| 5,116,309 | 5/1992 | Coll | 604/281 |
| 5,129,883 | 7/1992 | Black | 604/53 |
| 5,163,906 | 11/1992 | Ahmadi | 606/194 |
| 5,167,623 | 12/1992 | Cianci et al. | |
| 5,256,141 | 10/1993 | Gencheff et al. | 604/53 |
| 5,314,409 | 5/1994 | Sarosiek et al. | 604/45 |
| 5,320,604 | 6/1994 | Walker et al. | 604/96 |
| 5,328,470 | 7/1994 | Nabel et al. | 604/101 |
| 5,364,340 | 11/1994 | Coll | 604/281 |

*Primary Examiner*—Mark Bockelman
*Assistant Examiner*—N. Kent Gring
*Attorney, Agent, or Firm*—Kenyon & Kenyon

[57] ABSTRACT

A Vanarthos trauma urethral catheter includes a central portion located between proximal and distal ends of the catheter so that, when the catheter is in an operative position, the central portion extends within a patient's urethra. A plurality of openings extend through the surface of the central portion of the catheter to provide fluid communication between a first fluid channel formed within the catheter and the urethra. The catheter also includes a distal inlet which, when the catheter is in an operative position, is located within the bladder and provides fluid communication between the bladder and a second fluid channel formed within the catheter. The first fluid channel extends from the central portion of the catheter to a first proximal inlet formed in the proximal portion of the catheter and the second fluid channel extends from the distal inlet to a proximal outlet. The first proximal inlet and the proximal outlet are located outside the body of the patient when the catheter is in an operative position.

12 Claims, 4 Drawing Sheets

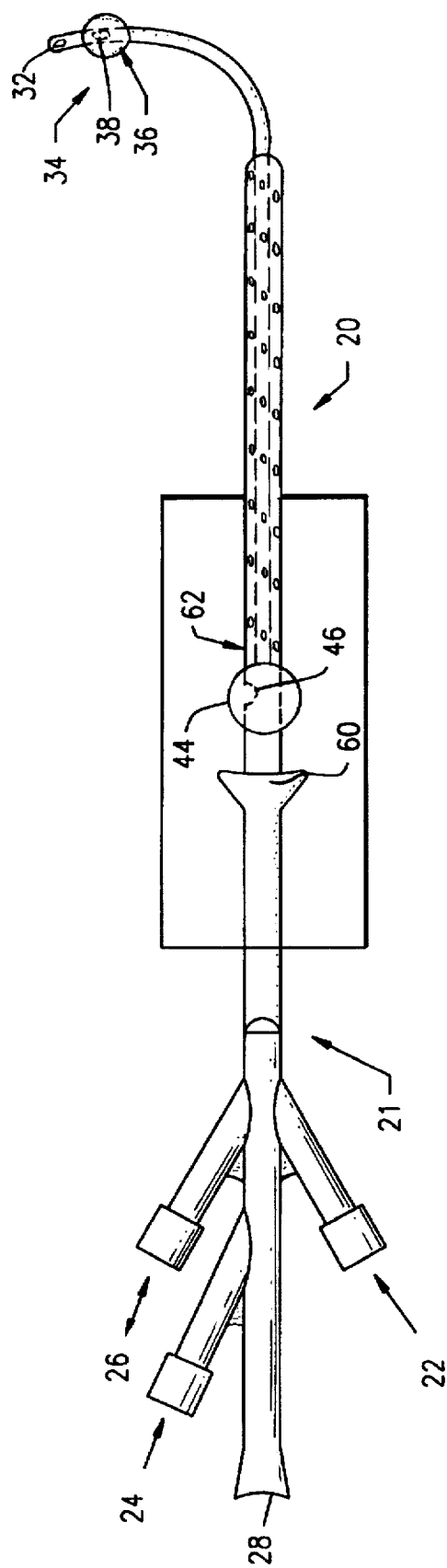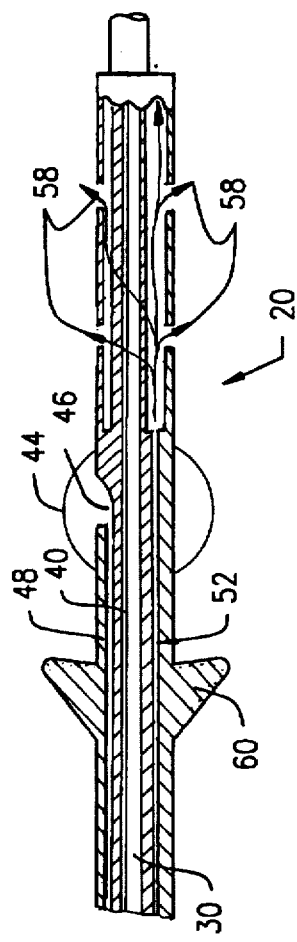
FIG. 2
FIG. 3

TRAUMA URETHRAL CATHETER AND METHOD OF USING SAME

This application is a continuation of application Ser. No. 08/325,107, filed on Oct. 17, 1994 now abandoned.

FIELD OF THE INVENTION

The present invention relates generally to catheters and relates more particularly to indwelling urethral catheters for use in performing a retrograde urethrogram (RUG) in a male patient.

BACKGROUND OF THE INVENTION

Foley catheters are introduced into the bladders of large numbers of trauma patients and inpatients substantially as shown in FIG. 1. A balloon 4 maintains the end 11 of the foley catheter 10 in position within the bladder 6. So that the bladder 6 may be regularly drained, the foley catheter 10 is usually left in place within the urethra for fear that it will be difficult to reintroduce the foley catheter 10 after it has been removed. When it is necessary to evaluate damage to the male urethra 8, an opaque contrast medium is introduced into the urethra prior to x-ray observation. This requires the insertion of a second reduced diameter catheter 12, such as a pediatric foley catheter, into the urethra alongside the indwelling foley catheter 10. A balloon 14 disposed around the reduced diameter catheter 12 is inflated to secure the reduced diameter catheter 12 in place so that the contrast medium may be distributed along the inner surface of the urethra 8. However, the presence of the foley catheter 10 often creates a non-uniform distribution of the contrast medium and leakage of the contrast medium. Consequently, it is often difficult to accurately evaluate the damage to the urethra 8. In addition, the placement of the second catheter 12 is a painful procedure which, because it must be done in a sterile manner, is time consuming and cumbersome.

SUMMARY OF THE INVENTION

The present invention is directed to a urethral catheter including a central portion located between the proximal and distal ends of the catheter so that, when the catheter is in an operative position, the central portion extends within a patient's urethra. A plurality of openings extending through the surface of the central portion of the catheter provide fluid communication between a first fluid channel formed within the catheter and the urethra. The catheter also includes a distal inlet which, when the catheter is in an operative position, is located within the bladder, providing fluid communication between the bladder and a second fluid channel formed within the catheter. The first fluid channel extends from the central portion of the catheter to a first proximal inlet formed in the proximal portion of the catheter and the second fluid channel extends from the distal inlet to a proximal outlet. Both the first proximal inlet and the proximal outlet are located outside the body of the patient when the catheter is in an operative position.

Thus, an RUG employing a Vanarthos trauma catheter according to the present invention may be performed without the use of a local anesthetic while the position of the various inlet ports in relation to the radiation field, decreases the radiation to which the operator's hands are exposed.

A Vanarthos catheter according to the present invention may also include an adjustable positioning cone which obviates the need for clamps that compress the penile urethra.

BRIEF DESCRIPTION OF THE DRAWINGS

FIG. 2 shows a side view of a Vanarthos trauma catheter according to the present invention;

FIG. 3 shows a partially cross-sectional side view of a proximal portion of a Vanarthos trauma catheter according to the present invention;

DETAILED DESCRIPTION

Figure 1:
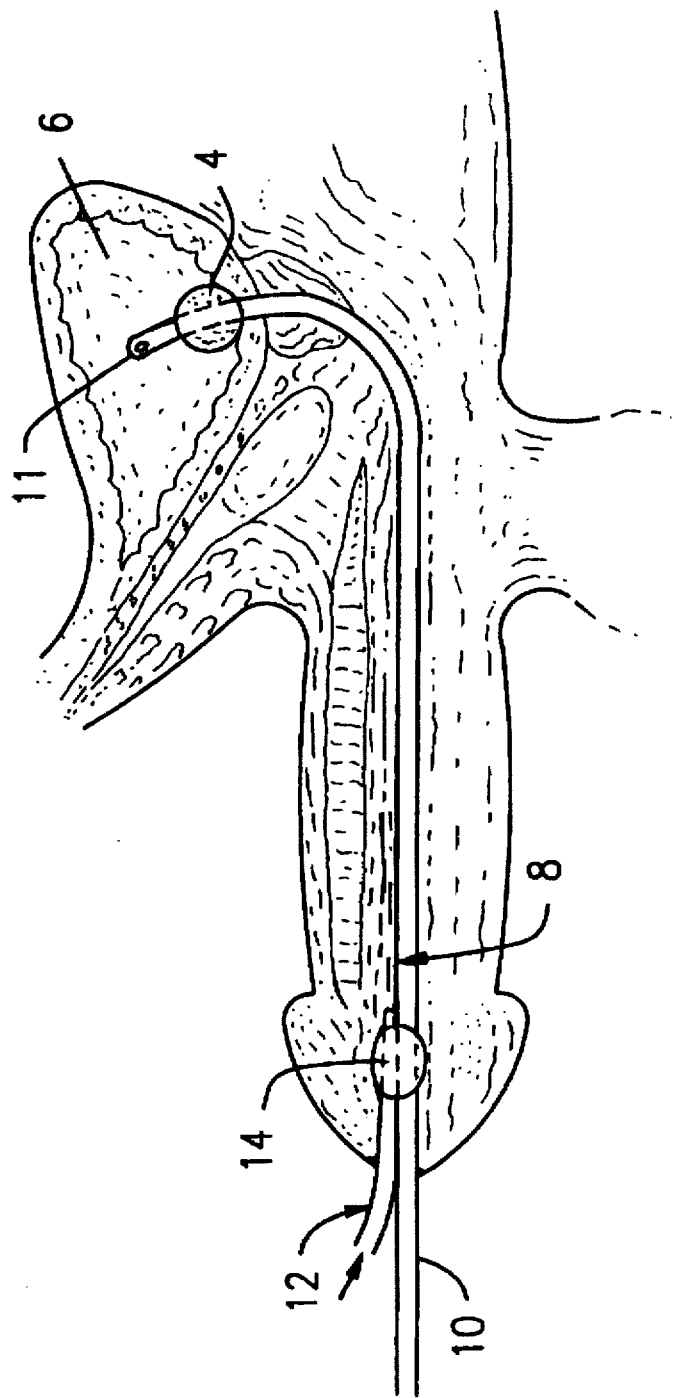
FIG. 1 shows a known foley catheter indwelling in the urethra with a second reduced diameter catheter inserted into the urethra alongside the foley catheter.
Figure 4:
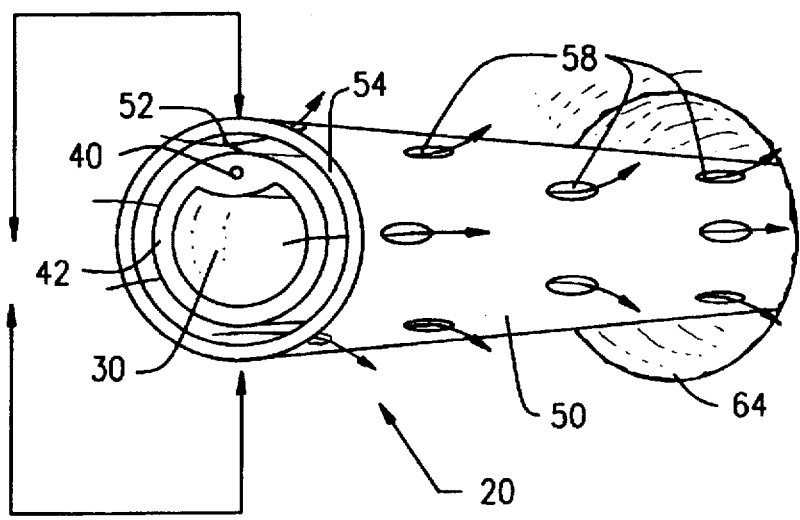
FIG. 4 shows a cross-sectional perspective view of an intermediate portion of a Vanarthos trauma catheter according to the present invention.
Figure 5:
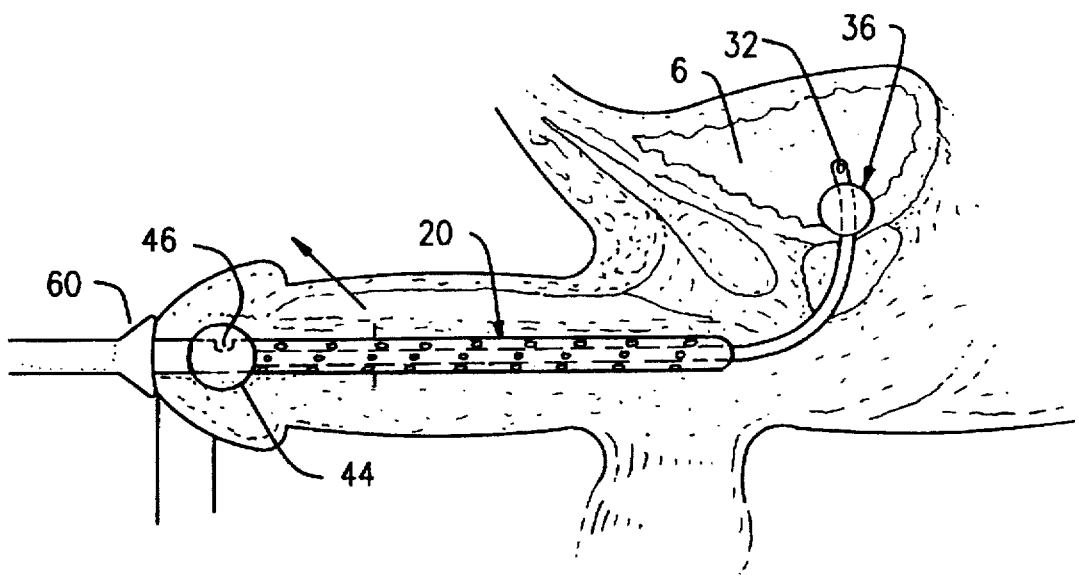
FIG. 5 shows a side view of a Vanarthos trauma catheter according to the present invention indwelling in the urethra.

Vanarthos trauma catheter 20 according to the present invention is shown in FIGS. 2–5. A proximal end 21 of the Vanarthos catheter 20 includes a first inlet 22, a second inlet 24 and a third inlet 26 as well as a proximal outlet 28. The proximal outlet 28 is in fluid communication with a first channel 30 formed within the Vanarthos catheter 20. The first channel 30 is preferably substantially centered in the Vanarthos catheter and extends from the proximal outlet 28 through the length of the Vanarthos catheter 20 to an inlet 32 at a distal end 34. A first balloon 36, which is received around a portion of the distal end 34 of the Vanarthos catheter 20, surrounds a distal outlet 38 which is in fluid communication with a second channel 40 which is formed within an annular wall 42 which surrounds the first channel 30. The second channel 40 extends from the distal outlet 38 to the third inlet 26. A second balloon 44 extends around a third outlet 46. The third outlet 46 is in fluid communication with a third channel 48, formed in an outer wall 50 of the Vanarthos catheter 20, which extends from the third outlet 46 to the second inlet 24. A fourth channel 52 extends from the first inlet 22 to an annular space 54 which surrounds an intermediate portion of the first channel 30. A portion of the outer wall 50 which surrounds the annular space 54 includes a plurality of openings 58. The openings 58, which are open to the outside of the outer wall 50, are preferably distributed substantially evenly about the entire circumference of the Vanarthos catheter 20.

When in an operative position, the proximal end 21 of the Vanarthos catheter 20 is located outside the body. The Vanarthos catheter 20 may include a positioning cone 60, the position of which is adjusted by the operator to locate the Vanarthos catheter 20 in a desired position. When in the desired position, a central portion 62 of the Vanarthos catheter 20, which extends from a distal end of the cone 60 to the distal end 34, is positioned within the urethral lumen and the distal end 34 extends into the bladder 6 so that the entire first balloon 36 is received within the bladder 6.

The diameter of the central portion 62 is preferably between 5.5 and 7.0 mm and more preferably between 6.0 and 6.5 mm while the diameter of the distal end 34 is preferably substantially the same as the diameter of known foley catheters, approximately 5.0 mm. The diameter of the second channel 40 and the third channel 48 may preferably be approximately 0.5 mm while the diameter of the first channel 30 may preferably be approximately 0.8 mm. Those skilled in the art will recognize that these diameters are limited by the desire to minimize the outside diameter of the portions of the Vanarthos catheter 20 which are to be received within the body while preserving the capacity of the Vanarthos catheter 20 to effectively drain contents of the bladder 6.

The RUG procedure, which is performed mainly in male patients, employing a Vanarthos catheter 20 is essentially the same for adults and children. With the patient supine, a catheter is passed through the urethra and into the bladder as is done with known Foley catheters. Air is then supplied to the third inlet 26 in order to inflate the first balloon 36, thereby anchoring the Vanarthos catheter 20 in position within the urethra. Thereafter, approximately 1 to 2 cc of air or saline is supplied via the second inlet 24, through the third channel 48, to the third outlet 46 to inflate the second balloon 44 within the fossa navicularis. When both the first balloon 38 and the second balloon 44 are inflated, the cone 60 is adjusted so that it is flush against the external meatus. The operator then supplies, under fluoroscopic guidance, a water soluble, non-viscous contrast medium, for example, Hypaque 45, to the fourth channel 52 via the first inlet 22 to the annular space 54. The contrast medium flows out of the openings 58 so that it is substantially evenly dispersed along the central portion 62 of the Vanarthos catheter 20 within the urethral lumen 64 to allow visualization of the anterior urethra. Steady injection of approximately 30–40 ml. of the contrast medium is continued to overcome the resistance of the external sphincter to permit visualization of the posterior urethra. The contrast medium may be pre-warmed to reduce the incidence of spasm of the external sphincter. Routine films of the urethra may then be taken including, for example, a supine posterior-anterior, and 30° oblique films to the right and to the left with the patient's leg abducted to the left and right, respectively, with the knee flexed.

Figure 6:
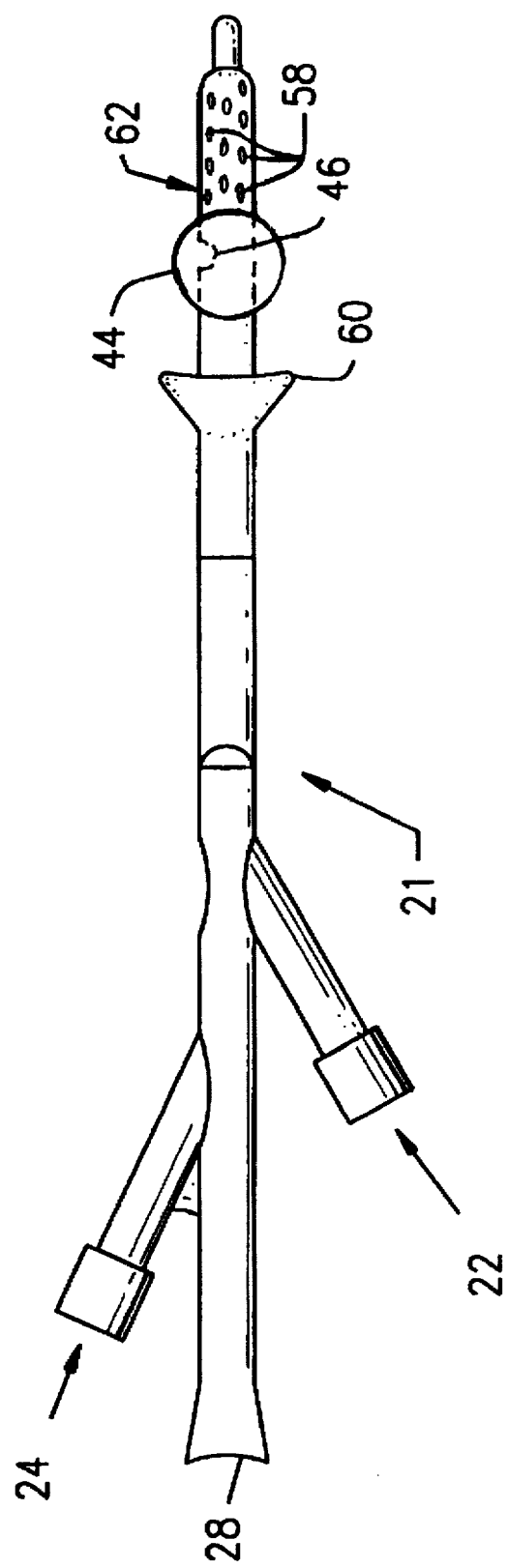
FIG. 6 shows a side view of a Vanarthos trauma catheter according to an alternate embodiment of the present invention.

As shown in FIG. 6, an alternative embodiment of the Vanarthos catheter 20 includes a proximal end 21 which is substantially similar to the previously described embodiment except that the third inlet 26 is omitted as the distal end of the catheter is not adapted to penetrate the bladder and there is no first balloon 36 to inflate. The catheter according to this embodiment is formed with a shortened central portion 62 and no distal portion 34. The shortened central portion 62 preferably extends approximately 2–3 cm. beyond the second balloon 46 located within the fossa navicularis. The shortened central portion 62 of this catheter also includes a plurality of openings 58 which are preferably substantially evenly spaced. As with the catheter according to the first embodiment, a second balloon 44 extends around the third outlet 46 of the shortened Vanarthos catheter 20. The use of the catheter 20 according to this embodiment is substantially the same as the use of the catheter 20 according to the first embodiment except that there is no inflation of the first balloon 36 to perform.

Those skilled in the art will recognize that a catheter according to this embodiment of the invention may be useful in evaluating injury to the urethral lumen in patients in whom an indwelling foley catheter is not necessary.

Those skilled in the art will recognize that the above-described embodiments of the present invention are for the purposes of illustration only and are not intended to limit the scope of the invention. It is understood that there are many modifications which may be made to the catheters described which will be apparent to those skilled in the art. These modifications are considered to be within the scope of the invention which is to be limited only by the claims appended hereto.

What is claimed is:

1. An urethral catheter including a proximal end and a distal end, wherein the catheter defines a longitudinal direction extending from the distal end to the proximal end and wherein, when the catheter is in an operative position, a distal portion of the catheter is located within a patient's bladder, a central portion of the catheter is located within the patient's urethra and a proximal portion of the catheter is located outside of the patient' body, the catheter comprising:

a first fluid channel within the catheter;

a plurality of openings extending through the surface of the central portion of the catheter to provide fluid communication between the first fluid channel and the urethra wherein the openings are dispersed substantially completely around the entire surface of the central portion of the catheter so that a fluid supplied to the first fluid channel is substantially evenly dispersed within the urethral lumen about the catheter;

a second fluid channel formed within the catheter;

a distal inlet formed in the distal portion of the catheter which provides fluid communication between the patient's bladder and the second fluid channel, wherein the first fluid channel extends in the longitudinal direction from the central portion of the catheter to a first proximal inlet formed in the proximal portion of the catheter and wherein the second fluid channel extends in the longitudinal direction from the distal inlet to a proximal outlet formed in the proximal portion of the catheter; and an inflation fluid channel formed within the catheter, wherein the inflation fluid channel extends in the longitudinal direction from a second proximal inlet formed in the proximal portion of the catheter to an intermediate outlet formed in a proximal end of the central portion of the catheter, the intermediate outlet being surrounded by a balloon coupling surface which, when the catheter is in the operative position, is located within the fossa navicularis.

2. An urethral catheter according to claim 1, wherein the catheter is substantially cylindrical and wherein the second fluid channel is substantially centrally located within the catheter and wherein the first fluid channel is formed in an annular space surrounding the second fluid channel.

3. An urethral catheter according to claim 1, further comprising a third fluid channel formed within the catheter, wherein the third fluid channel extends in the longitudinal direction from a third proximal inlet formed in the proximal portion of the catheter to a second distal outlet formed in the distal portion of the catheter and wherein the surface of the catheter adjacent to the second distal outlet is surrounded by a second balloon coupling surface which, when the catheter is in the operative position, is located within the patient's bladder.

4. An urethral catheter according to claim 3, wherein the catheter is substantially cylindrical and wherein the second fluid channel is substantially centrally located within the channel and wherein the first fluid channel is formed in an annular space surrounding the second fluid channel, and wherein the third fluid channel is formed within a wall separating the first and second fluid channels.

5. An urethral catheter according to claim 1, further comprising a positioning surface formed in the proximal portion of the catheter which, when the catheter is in an operative position, contacts the patient's external meatus to maintain the catheter in a desired operative position.

6. An urethral catheter according to claim 5, further including means for varying the position of the positioning surface relative to the distal end of the catheter.

7. An urethral catheter including a distal end and a proximal end, wherein the catheter defines a longitudinal direction extending from the distal end to the proximal end and wherein, when the catheter is in an operative position, a distal portion of the catheter is located within a patient's bladder, a central portion of the catheter is located within the patient's urethra and a proximal portion of the catheter is located outside of the patient' body, and wherein the catheter defines an outer surface, the catheter comprising:

a first proximal inlet formed in the proximal portion of the catheter;

a first fluid channel formed within the catheter;

a plurality of openings formed in the outer surface of the central portion of the catheter, wherein the openings extend through the outer surface of the catheter to provide fluid communication between the first fluid channel and the urethra, the first fluid channel providing fluid communication between the first proximal inlet and the openings, wherein the openings are dispersed substantially completely around the outer surface of the central portion of the catheter so that a fluid supplied to the first fluid channel is substantially evenly dispersed within the urethral lumen about the catheter;

a second proximal inlet formed in the proximal portion of the catheter;

an outlet formed in the central portion of the catheter so that, when the catheter is in an operative position, the outlet is located within the patient's fossa navicularis;

a second fluid channel formed within the catheter, wherein the second fluid channel extends from the second proximal inlet to the outlet, wherein the outlet is surrounded by a balloon coupling surface.

8. An urethral catheter according to claim 7, further comprising a positioning surface formed on the proximal portion of the catheter so that, when the catheter is in an operative position, the positioning surface contacts the external meatus to maintain the catheter in the desired operative position.

9. An urethral catheter according to claim 8, further comprising means for varying the position of the positioning surface relative to the distal end of the catheter.

10. A method of performing a retrograde urethrogram in a patient comprising the steps of:

inserting a catheter into the patient's urethra so that a central portion of the catheter, which is located between proximal and distal ends of the catheter, extends in a desired position within a patient's urethral lumen and so that a bladder drainage inlet at the distal end of the catheter is located within the patient's bladder, wherein the drainage inlet is in fluid communication with a proximal outlet outside the patient's body;

expanding the urethra in the fossa navicularis; and supplying a contrast medium to the urethral lumen via a plurality of openings extending through the surface of the central portion of the catheter; and imaging the urethra.

11. A method according to claim 10, further comprising the steps of:

before the catheter is inserted into the patient's urethra, coupling a first balloon to a distal portion of the catheter;

thereafter positioning the catheter in the patient's urethra so that the distal portion of the catheter is located within the patient's bladder; and after the catheter has been positioned within the patient's urethra, inflating the first balloon within the patient's bladder to maintain the catheter in the desired position within the urethra.

12. A method according to claim 10, further comprising the step of, before the catheter is inserted into the patient's urethra, coupling a second balloon to the central portion of the catheter, positioned on the central portion of the catheter so that when the catheter has been inserted into the patient's urethra, the second balloon is located within the patient's fossa navicularis, wherein the urethra in the fossa navicularis is expanded by inflating the second balloon.

* * * * *